United States Patent [19]

Dvorsky et al.

[11] Patent Number: 4,499,282

[45] Date of Patent: Feb. 12, 1985

[54] QUATERNARY AMMONIUM COMPOUNDS

[75] Inventors: Drahomir Dvorsky; Karel Cerovsky, both of Dvur Kralove nad Labem, Czechoslovakia

[73] Assignee: Vyzkumny ustav zuslechtovaci, Dvur Kralove nad Labem, Czechoslovakia

[21] Appl. No.: 516,147

[22] Filed: Jul. 21, 1983

Related U.S. Application Data

[62] Division of Ser. No. 354,494, Mar. 3, 1982, abandoned.

[30] Foreign Application Priority Data

Mar. 4, 1981 [CS] Czechoslovakia ............. 1537-81
Mar. 20, 1981 [CS] Czechoslovakia ............. 2050-81

[51] Int. Cl.$^3$ ............. C07D 405/06; C07D 405/14; C07D 233/60
[52] U.S. Cl. ............. 548/336; 544/224; 544/335; 544/374; 544/401; 548/341; 548/378; 548/379
[58] Field of Search ............. 548/336, 341

[56] References Cited

U.S. PATENT DOCUMENTS 3,435,049  3/1969  Hoffer ............. 548/336 X
3,792,018  2/1974  Logan ............. 548/336 X
3,991,202  11/1976 Janssen et al. ............. 548/336 X
4,127,489  11/1978 Pracht et al. ............. 548/341 X Primary Examiner—Richard A. Schwartz

[57] ABSTRACT

Quaternary ammonium compounds suitable for use in finishing cellulose fiber containing textile material are described. The compounds are of the general formula

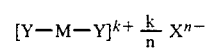

wherein
k is an integer of 1-2,
n is an integer of 1-3,
X is an anion of a strong acid, and
Y is selected from among

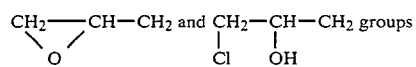

which are bound to the nitrogen atoms of a heterocyclic compound, n, which is a 5 or 6 membered ring.

1 Claim, No Drawings

QUATERNARY AMMONIUM COMPOUNDS

This application is a division of application Ser. No. 354,494, filed Mar. 3, 1982, now abandoned.

This invention relates to novel quaternary ammonium compounds and to a method for the preparation thereof. More particularly, the present invention relates to quaternary ammonium compounds suitable for cationizing polymeric materials and, specifically, for finishing cellulose containing textile fabrics.

Heretofore, it has been common practice in finishing processes to modify cellulose fibers with quaternary ammonium compounds. This treatment is found to enhance the dyability of the cellulose and to increase dye fastness. Typically, such compounds have been reactive quaternary ammonium salts derived from tertiary amines and epichlorohydrin.

Studies of the known reactive quaternary ammonium compounds designed for mediating the dyeing of cellulose fibers by anionic dyes warrant the conclusion that using these compounds, the so-called cationization agents, from a commercial standpoint will increase significantly. These compounds react in alkaline media with the hydroxyl groups of cellulose to yield a covalent bond, so permitting the quaternary ammonium group to bond ionically with an anionic dye.

The cationization agents employed heretofore have generally been of the formulae

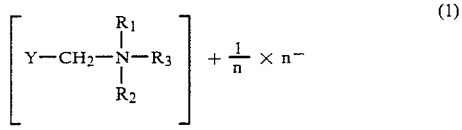

and

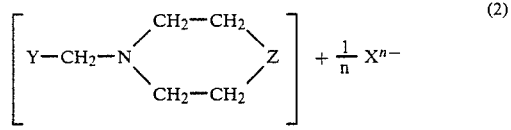

wherein

R$_1$ and R$_2$ represent alkyl or hydroalkyl groups having from 1 to 3 carbon atoms, R$_3$ is an alkyl, phenyl or alkylaryl group, Z is an oxygen atom or a methylene group (CH$_2$), Y is selected from among

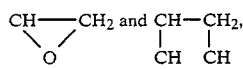

X is an anion of a strong organic or inorganic acid, and n is an integer of 1-3.

The foregoing compounds are of interest since they permit higher dye utilization in a subsequent dyeing process while simultaneously enhancing dye fastness, reducing the demand for operation water and contributing to the simplification of the dyeing process.

The quaternary ammonium compounds employed heretofore possess only one reactive (Y) group which permits them to bind anionic dyes upon cellulose. However, these compounds cannot simultaneously find other finishing agents or cross-link cellulose.

In accordance with the present invention, novel quaternary ammonium compounds are described, such compounds being of the formula

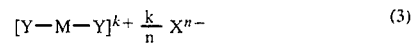

wherein k is an integer of 1 or 2, n is an integer of 1 to 3,

X is an anion of a strong acid, and y is selected from among

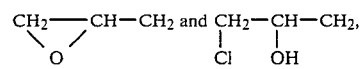

Y being bound to nitrogen atoms of a heterocyclic compound M which comprises a five or six-membered ring having two nitrogen atoms. The heterocyclic compound may be selected from the group comprising compounds derived from pyridazine, pyrazine, pyrimidine, piperazine, pyrazol, pyrazoline, pyrazolidine and imidazol wherein the individual atoms of the heterocycle may contain a substituent selected from among hydrogen an alkyl or a hydroxyalkyl group having from 1–4 carbon atoms.

Compounds within the scope of formula 3 evidence the same level of characteristics as the monofunctional compounds of formulae 1 and 2 in the dye processes. Additionally, the presence of two reactive groups (Y) enhances the utilization of the agents and enables them to be employed in certain technologies wherein the monofunctional agents are not suitable.

The compounds described herein are capable of reacting with two hydroxyl groups of cellulose and in so doing effect cross-linking thereof. They are also capable of reacting with dialkyl, alkyl or amine groups of a dye and simultaneously with a cellulose hydroxyl group. Thus, it is possible to obtain simultaneously in a single step a high level of dyeability in addition as well as a no-iron or creaseproof finish. It is also possible by means of a suitable dispersion dye to dye the two components of a blend of polyester and cellulose fibers.

It is an object of the present invention to provide a method for preparing quaternary ammonium compounds of the general formula 3 wherein Y represents

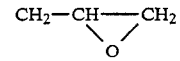

wherein a heterocyclic compound selected from the group comprising pyridazine, pyrazine, pyrimidine, piperazine, pyrazol, pyrazoline, pyrazolidine, imidazol, alkyl derivatives and hydroxyalkyl derivatives thereof in which alkyl or hydroxyalkyl has a maximum of four carbon atoms is permitted to react with epichlorohydrin. These heterocyclic compounds have a 5 or 6 membered ring with two nitrogen atoms in the ring. Heterocyclic compounds suitable for this purpose are set forth in Table I which follows. Compounds of formula 3 may conveniently be prepared by the direct reaction between epichlorohydrin and one of the noted heterocyclic compounds. Following the reaction, the two nitrogen atoms possess a positive charge.

TABLE I

Examples of heterocyclic compounds for which the symbol M stands in the formula 3

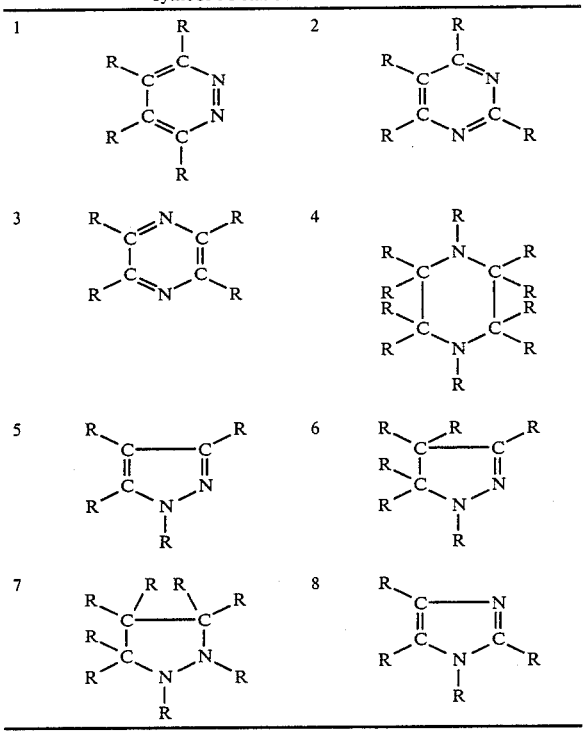

R is a hydrogen atom, or an alkyl group with one to four carbon atoms.

It is also an object of the present invention to prepare quaternary ammonium compounds of formula 3 wherein X represents

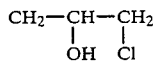

wherein an aqueous solution of a salt obtained by reaction of a strong acid with a heterocyclic compound selected from the group comprising pyridazine, pyrazine, pyrimidine, piperazine, pyrazol, pyrazoline, pyrazolidine, imidazol, alkyl derivatives and hydroxyalkyl derivatives thereof in which the alkyl or hydroxyalkyl has a maximum of four carbon atoms reacts with epichlorohydrin. Salts of heterocyclic compounds react with epichlorohydrin and may be dissolved in water or a non-aqueous polar solvent. Following reaction, the two nitrogen atoms possess a positive charge. The heterocyclic compounds suitable for this purpose are set forth in Table I.

The quaternary ammonium compounds of formula 3 are designed for finishing cellulose containing textile materials. In accordance with the finishing technique of this invention, cellulose fibers are modified by the quaternary ammonium compounds of formula 3 to enhance their dyeability and dye fastness and to effect cross-linking of cellulose.

Typical examples of the quaternary ammonium compounds of formula 3 are set forth in Table II. It will be understood by those skilled in the art that these examples are illustrative only, and do not limit the scope of the invention.

TABLE II

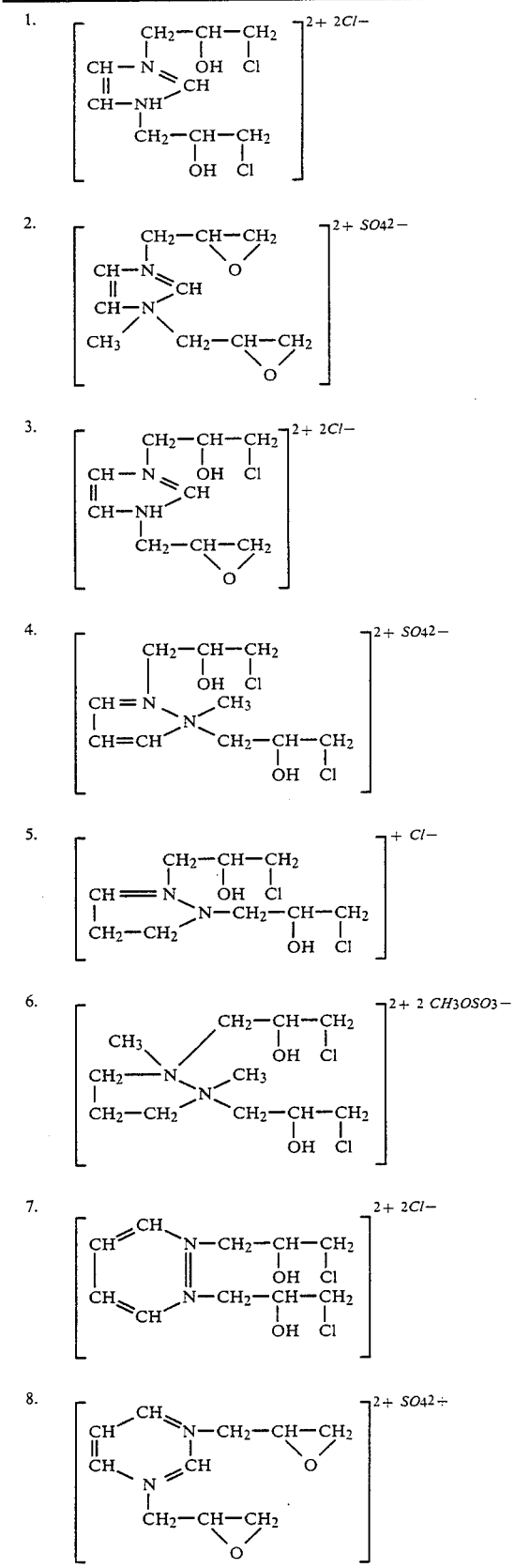

TABLE II-continued

9. 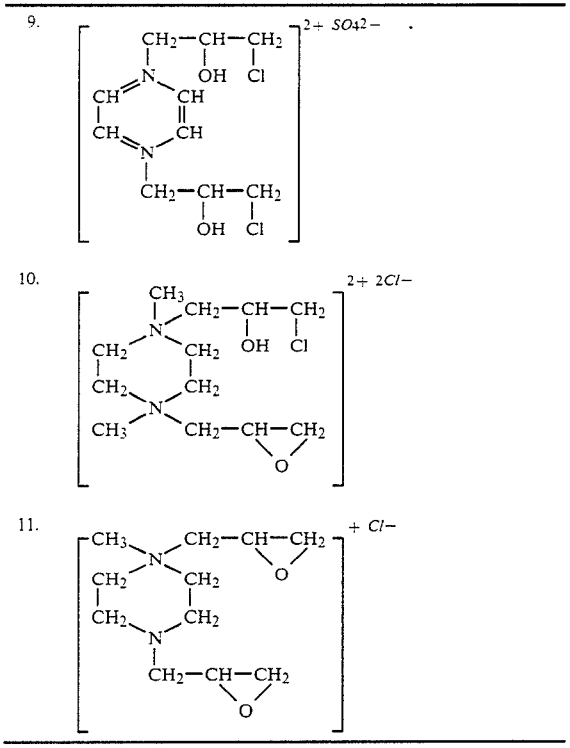

10.

11.

Compounds having the

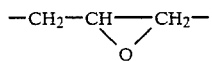

reactive group in accordance with the invention may be prepared by reacting epichlorohydrin and a heterocyclic compound having two nitrogen atoms (as exemplified in Table I). Thus, for example, N,N-dimethylpiperazine reacts with epichlorohydrin as follows:

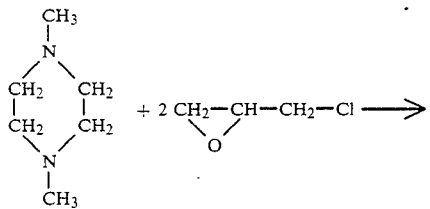

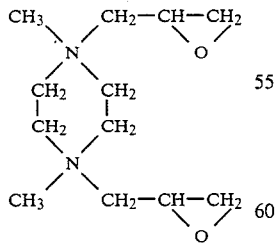

The effect of the quaternary ammonium compounds of general formula 3 on cellulose fibers containing textile materials may be promoted by preimpregnating the textile with an aqueous sodium hydroxide solution in a concentration ranging from 150–350 g/liter.

Compounds having the

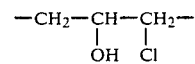

reactive group in accordance with the invention may be prepared by exposing aqueous solutions of salts of heterocyclic compounds to the action of epichlorohydrin as follows:

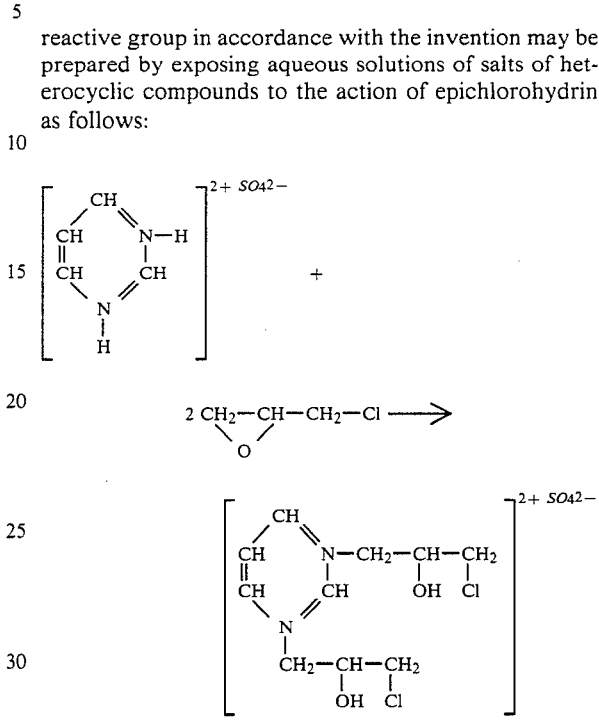

Five membered ring compounds can be prepared, for example, from imidazol in an aqueous medium in accordance with the following equation:

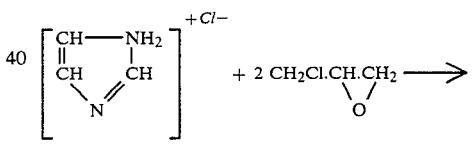

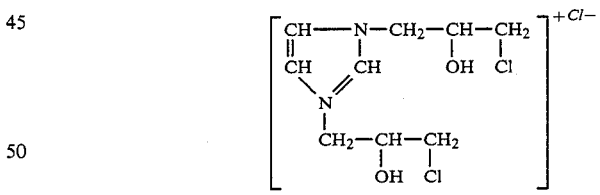

or in the medium of a non-aqueous polar solvent

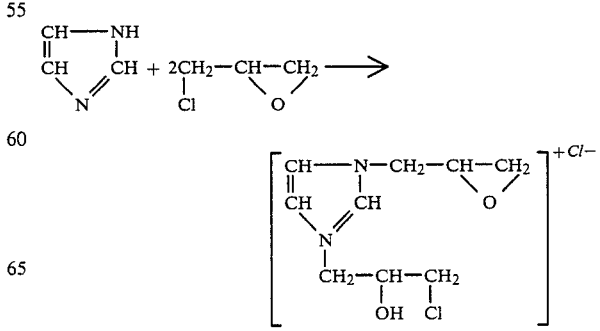

The use of compounds of formula 3 before and during the dyeing process has been found to result in the enhancement of dye fastness values and dye utilization. A post dyeing application with such compounds results solely in an improvement in dye fastness. However, textile material recovery is not dependent upon the fixation sequence, that is, before, during or after the dyeing process.

It has also been noted that wet material recovery is enhanced when reaction between the compound and cellulose fibers is effected in a swollen or wet condition. And, an increase in crease resistance and dry recovery is caused by those processes which make use of a drying sequence.

As noted above, a particularly marked effect with compounds of formula 3 is obtained when the cellulose material is pre-impregnated with an aqueous liquor containing from 150-350 g/liter of sodium hydroxide and then treated, without an intermediate washing step, with a solution of the compounds. These compounds (of formula 3) may be used for treating not only pure cellulosic materials but also blends thereof with synthetic materials such as polyamide, polyester and polyacrylonitrile fibers.

In practicing the present invention, it is also feasible to dye blends of synthetic fibers, for example, polyesters, with cellulose by the use of dispersion dyes in the so-called thermosol process wherein a dye containing an amino group is bonded with a cellulose fiber by a bridge comprising a compound of formula 3. Still further, the compounds of formula 3 may be employed as promoters for the dyeing process or as cross-linking agents to be used in specific finishing steps.

The cellulose materials may be treated with alkali solutions of the compounds of the invention before, during or after the dyeing process. Typical procedures are as follows:

Prior to dyeing, the cellulose containing fabrics are exposed to compounds of formula 3 in long liquors at temperatures ranging from 30°-60° C., or, preferably, by the use of an impregnation step wherein the reaction with the cellulose fibers takes place in an alkaline medium by maturing the fabric in batch at a temperature ranging from 20°-30° C. (the maturing period being universely proportional to the temperature). Alternatively, the reaction may be accelerated by passing the fabric through a vapor or by drying at a temperature ranging from 100°-230° C. for a short time period.

The concentration of formula 3 compound may range from 5 to 100 g/liter. Suitable alkali material may be sodium hydroxide having a concentration ranging from 2 to 50 grams per liter. If the compounds are fixed in dry condition at temperatures less than 180° C. it is possible to employ ammonia liberating compounds such as hexamethylene tetramine. Compounds including a reactive epoxide group react with cellulose at such temperatures in the absence of alkali.

Studies have also revealed that the compounds can be employed simultaneously with anionic dyes. Thus, they may be used with reactive dyes in an impregnation dyeing process with batch maturation fixation or fixation with dry heat or vapor wherein there results an enhancement in dye utilization. This constrast sharply with the prior art compounds of formulae 1 and 2 which cannot be used for one-bath dyeing in combination with reactive dyes.

The foregoing principles also apply with respect to utilization of the compounds of the invention in textile printing, and finishing processes.

Several examples of the present invention are set forth below. It will be appreciated by those skilled in the art that these examples are solely for purposes of exposition and are not to be construed as limiting.

EXAMPLE 1

80 kg. of pyrimidine was placed in a 600 liter enamelled jacketed kettle adapted with a reflux condenser and an agitator, and heated to 25° C. While cooling, 200 kg of 36 percent hydrochloric acid was next added. After the total amount of acid had been added, the kettle was cooled to a temperature of 20° C. During the following 3 hours 184 kg of epichlorohydrin was added to the kettle while simultaneously cooling to prevent a temperature rise over 50° C. The temperature was then allowed to rise to 85° C. The reaction was maintained at this temperature for another 60 minutes whereupon the kettle content was cooled to 25°-30° C. The aqueous solution remaining after the reaction contained about 70% of 1,3-di-(3-chloro-2-hydroxypropyl) pyrimidinium chloride.

EXAMPLE 2

Into a three-neck glass flask provided with a reflux condenser, an agitator and a thermometer there were placed 82 g of 1-methylimidazol and 552 g epichlorohydrin. Then, the temperature was gradually raised to 90° C. and maintained thereat for 8 hours. During this period, 1,3-di-(2,3-epoxypropyl)-3-methylimidazolinium chloride began to precipitate in crystal form. After the reaction had been terminated, the product was filtered off and washed with acetone on the filter. The yield amounted to 90% of theoretical.

EXAMPLE 3

In a glass flask similar to that described in Example 2, of glacial acetic acid were mixed. Then, 68 g imidazol were gradually added to the flask. The flask jacket was next cooled to 50° C. and after 3 hours 184 g epichlorohydrin was added with simultaneous cooling to prevent a temperature rise over 60° C. After the total amount of epichlorohydrin had been added, the temperature was allowed to rise to 90° C. and the reaction mixture temperature was maintained at this level for another 60 minutes. The reaction mixture contained 76% of 1,3-di-(3-chloro-2-hydroxypropyl) imidazolinium acetate.

EXAMPLE 4

A cotton shirting pretreated and mercerized was impregnated in a padder by a bath containing
  40 g/liter of the compound No. 1 from Table 2
  20 g/liter of sodium hydroxide,
at a bath temperature of 20° C. and 80 percent pick-up.

After the passage through the padder, the fabric was rolled on to a large-diameter batch roll. In this form it was allowed to mature for 8 hours.

The fabric was then washed in a jigger and neutralized by acetic acid up to pH of 6-7.

The process was followed by dyeing with
  3% Reactive Blue C.I. 5
at a dye bath temperature of 80° C. for 40 minutes. Then, the fabric was washed for 10 minutes with water (50° C.). The dyeing process did not require other admixtures, or a conventional final soaping step. The resulting deep blue shade exhibited very good wet fastness values. It was determined that the angles of recovery with the wet fabric were at least 130° C. in the two directions.

Similar results were obtained employing the following compounds set forth in Table 2:
compound No. 2
compound No. 3
compound No. 4
compound No. 5

The same result was attained using the following dyes:
Reactive Red—C.I. 2,8,11,13,9,29,4,58,16
Reactive Yellow—C.I. 7,12,81,3,2,6,18,22
Reactive Blue—C.I. 4,14,49,2,46,39,71,109
Reactive Brown—C.I. 2,23,10,17,7,1
Reactive Orange—C.I. 5,35,2,13,4,1
Reactive Black—C.I. 8,5,1,9

EXAMPLE 5

Cotton yarn on cross-wound bobbins was treated for 45 minutes in a cheese dyeing machine at a liquor ratio of 1:5 and a temperature of 60° C. with a bath containing
25 g/liter of compound No. 3 from Table 2 and
15 g/liter of sodium hydroxide
Then, the bobbins were washed, neutralized and dyed in the same machine using
1.5% Direct Red C.I. 80.
Initially, the dyeing temperature was 30° C. The bath was then heated within 30 minutes to 90° C. and the dyeing continued at this temperature for another 10 minutes. The resulting color evidenced good wet fastness values.

The same result was attained using for cationization the following compounds chosen from Table 2:
compound No. 1
compound No. 2.

The final color evidenced good wet fastness values and the wet fabric exhibited excellent angles of recovery.

EXAMPLE 8

A fabric from a polyester/cotton blend (67/33) was impregnated in a padder (65% pick-up) with a bath containing
40 g/liter of compound No. 6 from Table 2
25 g/liter of Dispersion Blue C.I. 73 and
4 g/liter of sodium alginate.
After having been dried at 100° C. in a hotflue passage, the fabric was treated for 60 seconds by passing through a thermosol hotflue. The dyeing process was then terminated by passage through an open-width washing machine. The two components of the blend were evenly covered. The fabric evidenced good crease resistance.

EXAMPLE 9

A fabric printed with substantive dyes
Direct Yellow—C.I. 29
Direct Orange—C.I. 39
Direct Blue—C.I. 71
Direct Red—C.I. 80,
after washing out a thickener and being dried, was impregnated in a padder with a bath containing
25 g/liter of Compound No. 3 from Table 2 and
20 g/liter of sodium carbonate.
Without having been subjected to intermediate drying, the fabric was steamed for 10 minutes in a passage through a steamer (saturated steam at a temperature of from 102° to 105° C.). After an alkali excess had been washed out, the print fixation and no-iron finish were terminated.

For dyeing the following dyes were employed:
Direct Yellow—C.I. 29
Direct Orange—C.I. 39
Direct Blue—C.I. 71
Direct Brown—C.I. 218
Direct Black—C.I. 56

EXAMPLE 6

A fabric made from a polyester and viscose fiber blend (70/30) was impregnated with the bath employed in Example 4. After maturation, the fabric was washed and neutralized in a rope dyeing machine. In the same machine, the fabric was then dyed (1:7 liquor ratio) using
2.0% Dispersion Orange—C.I. 31
0.7% Reactive Orange—C.I. 13.
The initial dye bath temperature of 60° C. was elevated within 30 minutes to 125° C. and maintained for another 40 minutes. Then, the bath was cooled to 80° C. for 45 minutes and the fabric washed with water at the same temperature for 10 minutes. By gradual addition of cold water, the dyed fabric was cooled to 30° C.

The resulting color evidenced good fastness values and the fabric exhibited very good no-iron characteristics.

EXAMPLE 7

A linen fabric was impregnated in a padder with a bath containing
50 g/liter of compound 4 from Table 2
25 g/liter of sodium hydroxide
100 g/liter of urea and
15 g/liter of Direct Red C.I. 76
(70% pick-up, dye bath temperature: 20°–25° C.).

EXAMPLE 10

A fabric cationized as described in Example 1 was printed with a printing paste containing
500 g/kg of an alginate thickener
20 g/kg of Reactive Blue C.I. 4 and
50 g/kg of urea.
After drying, the print was steamed for 10 minutes with saturated steam at a temperature of from 102° to 105° C. The process was terminated by a passage through an open-width washing machine.

The print was characterized by high fastness values and very good dye utilization.

We claim:
1. Quarternary ammonium compound of the formula

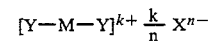

wherein k is an integer of 1–2,
n is an integer of 1–3,
X is an anion of a strong acid, and
Y is selected from the group consisting of

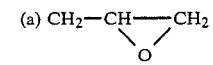

and (b) 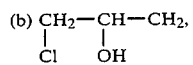
said group being bound to the nitrogen atoms of an imidazole ring M, the individual atoms of the imidazole having bound thereto at least one substituent selected from the group consisting of hydrogen, and alkyl groups having from 1-4 carbon atoms.
* * * * *